, , , 
United States Patent [19]

Bhaduri et al.

[11] Patent Number: 4,464,295
[45] Date of Patent: Aug. 7, 1984

[54] SIMPLE AND RAPID METHOD FOR EXTRACTION OF PROTEINS FROM BACTERIA

[75] Inventors: Saumya Bhaduri, Warminster; Paul H. Demchick, Penn Valley, both of Pa.

[73] Assignee: The United States of America as represented by the Secretary of Agriculture, Washington, D.C.

[21] Appl. No.: 524,179

[22] Filed: Aug. 17, 1983

[51] Int. Cl.$^3$ .............................................. C07G 7/00
[52] U.S. Cl. .................................. 260/112 R; 424/92; 424/177
[58] Field of Search ...................... 260/112 R; 424/92

[56] References Cited

U.S. PATENT DOCUMENTS

| | | | |
|---|---|---|---|
| 3,686,144 | 8/1972 | Tamura et al. | 260/112 R X |
| 3,718,541 | 2/1973 | Kalina | 260/112 R X |
| 3,962,466 | 6/1976 | Nakabayashi | 260/112 R X |

Primary Examiner—Howard E. Schain
Attorney, Agent, or Firm—M. Howard Silverstein; William E. Scott; David G. McConnell

[57] ABSTRACT

44A simple, rapid method for extracting proteins from pathogenic and nonpathogenic bacteria is described.

3 Claims, No Drawings

SIMPLE AND RAPID METHOD FOR EXTRACTION OF PROTEINS FROM BACTERIA

BACKGROUND OF THE INVENTION

1. Field of The Invention

This invention pertains to a simple and rapid method for extraction of proteins from both pathogenic and nonpathogenic bacteria. More particular, it pertains to a method of extracting proteins from bacteria that is safe, that is applicable to a broad spectrum of bacteria, that reduces problems of containment and aerosol generation, that does not require special equipment, that is inexpensive, that is reproducible and that can be used easily to process a large number of different size samples.

2. Description of The Art

A variety of methods including both mechanical and enzymatic disruption of bacterial cells is available to prepare cell-free extracts. Mechanical disruption techniques include sonication, blending or grinding with abrasives, agitation with glass beads, or use of a French press. Enzymatic methods including autolysis and chemical treatments have also proven useful in specific instances. The choice of a specific extraction procedure is dependent on the particular species or strain of microorganism being studied, the quality of protein required, and the type of analyses to be performed.

SUMMARY OF THE INVENTION

An object of this invention is to provide a simple and rapid method for extracting proteins from pathogenic and nonpathogenic bacteria.

Another object of this invention is to provide a method of extracting proteins from bacteria that is safer and superior to known methods.

Still another object of this invention is to provide a method of extracting proteins from bacteria that is applicable to a broad spectrum of bacteria and that does not require special equipment.

A still further object of this invention is to provide a method that is inexpensive and reproducible and that can be used easily to process a large number of samples.

According to this invention the above objects are accomplished by a method wherein the cells are treated with a suitable solvent such as acetone for a short period of time, the cells collected by centrifugation, volatile residues removed, and the proteins extracted with an aqueous phase solvent.

DESCRIPTION OF THE INVENTION

Preparation of cell-free extracts of pathogens presents unique difficulties. Mechanical disruption techniques are not always applicable because of potential biohazard problems associated with contamination of equipment and generation of aerosols. Use of lytic enzymes avoids this problem. However, their addition to a cell extract may increase the complexity of subsequent protein isolations. Furthermore, many gram-positive bacteria are resistant to the action of lysozyme and other available bacteriolytic enzymes.

The method of this invention has been successfully and safely employed for the extraction of cellular proteins suitable for biochemical analyses from a variety of bacterial species including gram-positive pathogens. The method is reproducible, easy, rapid, and can be used to process a few samples or a large number of samples. One of the special uses for which we have employed the method of this invention is to characterize the proteins from *Clostridium botulinum* type C. Estimation of protein and polyacrylamide gel electrophoresis showed that protein composition of extracts made by a method of this invention were comparable with those prepared by established methods such as sonication and agitation with beads.

Strains of *Staphylococcus aureus, Escherichia coli,* and *Bacillus cereus* were grown without agitation for 24 hours at 37° C. in Brain Hear Infusion (BHI). *Clostridium botulinum* was grown anaerobically at 37° C. for 24 hours in BHI supplemented with 1% arginine to delay autolysis. Cells from 20 ml. of culture were harvested by centrifugation (7000×g), washed twice with phosphate buffered saline (PBS) solution without $Mg^{2+}$ and $Ca^{2+}$, and recentrifuged. The cells were then resuspended in 10 ml. of ice-cold acetone (analytical grade), allowed to stand on ice for five minutes, and collected by centrifugation (7000×g). Experiments demonstrated that acetone treatment for five minutes was sufficient. Treatment for longer periods of time did not change the efficiency of protein extraction. Residual acetone was removed under a stream of nitrogen, and the proteins were then extracted by incubating with 1.0 ml. of 1% sodium dodecyl sulfate (SDS) for two minutes. The acetone pretreatment was found necessary since the direct utilization of detergents did not extract cellular proteins from gram-positive bacteria.

In order to compare methods, we prepared extracts by sonication and glass bead disruption. We did this by using PBS-washed *S. aureus* 184 cells that were resuspended in 1% SDS such that the bacterial cell concentration was 20 times that of original culture. One portion of the suspension was agitated vigorously with about 0.1 mm glass beads for 15 minutes with ice-water cooling. Another portion was treated ultrasonically, intermittently, with ice-water cooling, as described in J. Biol. Chem 249, 634-644, 1974. The extracts were clarified by centrifugation (7000×g), and the supernatants used for protein estimation and SDS-polyacrylamide gel electrophoresis (SDS-PAGE). Longer or more vigorous sonication or agitation with beads was found not to increase substantially the amount of protein extracted or change the SDS-PAGE profile.

The yield of protein for the acetone-SDS extraction technique and that for the sonication was 200 mg protein/g dry weight of cells, while the bead agitation technique yielded 175 mg/g. This indicates that the efficiency of the acetone-SDS extraction technique is equivalent to that of the other techniques. SDS-PAGE patterns of the protein extracts from the three techniques were obtained. The electrophoretic pattern of the acetone-SDS method resembled those obtained by sonication and agitation with glass beads, again indicating that the acetone-SDS method produces cell extracts equivalent to those produced by the other techniques. The protein extracted per mass of dry cells from all of the species tested by the method of this invention is shown in Table 1. Adequate protein profiles were readily obtained with all of the tested species, suggesting that the extraction technique is applicable to a variety of bacterial species and that it is applicable to proteins having a wide range of molecular weight.

The experimental evidence shows that the acetone-SDS extraction technique of this invention produces cellular protein preparations equivalent to those produced by other techniques. Furthermore, the present technique offers some distinct advantages since it does not require special equipment; does not involve the generation of aerosols, that is, it can be used with pathogens; does not add extraneous proteins to the samples; and can be used effectively with a variety of bacterial species. The invention is an inexpensive, rapid, reproducible method for preparing large numbers of cellular protein samples regardless of pathogenicity. We also found that the method can be scaled up or down for any volume between one ml. to one liter of culture.

Although we used acetone to treat the cells, nitrogen to remove volatile residues, and sodium dodecyl sulfate to extract the proteins, the invention is not meant to be limited to these particular materials. Organic solvents other than acetone could most likely be used for the same purpose, other inert gases could be used in place of nitrogen and other aqueous phase solvents can be used instead of sodium dodecyl sulfate.

TABLE 1

| Species | Strain # | mg protein extracted per gram dry weight of cells |
|---|---|---|
| *Staphylococcus aureus* | 184 | 200 |
| *Staphylococcus aureus* | 196E | 200 |
| *Clostridium botulinum* | type C/ A028 | 150 |
| *Escherichia coli* | 20S0 | 225 |
| *Bacillus cereus* | 5065 | 200 |

We claim:

1. A method of extracting proteins from bacteria comprising treating bacterial cells with a suitable volatile organic solvent for about five minutes, centrifuging the treated cells and the solvent to collect the cells, removing the volatile residues from the collected cells with a stream of inert gas, and extracting the proteins from the cells with an aqueous phase solvent.

2. The method of claim 1 wherein the solvent is acetone and the aqueous phase solvent is sodium dodecyl sulfate.

3. A method of extracting proteins from bacteria comprising suspending the bacterial cells in ice-cold acetone for about five minutes, centrifuging the suspension to collect the cells, removing residual acetone with a stream of nitrogen, and extracting the protein with sodium dodecyl sulfate.

* * * * *